United States Patent
Gormley et al.

(10) Patent No.: US 8,673,276 B2
(45) Date of Patent: Mar. 18, 2014

(54) COMPOSITION AND METHOD FOR THERMALLY ACTIVATED HAIR TREATMENT

(75) Inventors: John Gormley, Midland Park, NJ (US); David Granatell, Elmwood Park, NJ (US); Glenn Baird, Rockaway, NJ (US)

(73) Assignee: Grant Industries, Inc., Elmwood Park, NJ (US)

( * ) Notice: Subject to any disclaimer, the term of this patent is extended or adjusted under 35 U.S.C. 154(b) by 107 days.

(21) Appl. No.: 13/193,799

(22) Filed: Jul. 29, 2011

(65) Prior Publication Data

US 2012/0031420 A1    Feb. 9, 2012

Related U.S. Application Data

(60) Provisional application No. 61/370,831, filed on Aug. 5, 2010.

(51) Int. Cl.
*A61Q 5/04* (2006.01)
(52) U.S. Cl.
USPC ...................... 424/70.12; 424/70.2
(58) Field of Classification Search
None
See application file for complete search history.

(56) References Cited

U.S. PATENT DOCUMENTS

| | | | | |
|---|---|---|---|---|
| 5,409,695 A | * | 4/1995 | Abrutyn et al. | 424/70.12 |
| 5,468,477 A | * | 11/1995 | Kumar et al. | 424/78.17 |
| 5,935,560 A | * | 8/1999 | Seper et al. | 424/70.12 |
| 2004/0082717 A1 | * | 4/2004 | Van Dyke et al. | 525/54.1 |
| 2010/0254924 A1 | * | 10/2010 | Hamilton et al. | 424/62 |
| 2011/0229430 A1 | * | 9/2011 | Hawkins et al. | 424/70.12 |

FOREIGN PATENT DOCUMENTS

WO    WO 99/26591    *    6/1999

* cited by examiner

*Primary Examiner* — Jyothsna Venkat
(74) *Attorney, Agent, or Firm* — Jonathan Myers; Andrew Wilford

(57) ABSTRACT

A formulation is disclosed useful for semi-permanent, thermal conditioning and styling of the hair comprising a mercaptosilicone polymer derived from greater than 25 mole percent mercaptosilicone monomer. A method of straightening the hair is also disclosed which comprises the steps of applying the mercaptosilicone polymer formula to the hair and then styling the hair at an elevated temperature with a flat iron to achieve a lasting straight style that remains after more than one shampoo cycle.

4 Claims, No Drawings

COMPOSITION AND METHOD FOR THERMALLY ACTIVATED HAIR TREATMENT

CROSS REFERENCE TO RELATED APPLICATIONS

This application is related to U.S. Provisional Application Ser. No. 61/370,831 filed 5 Aug. 2010.

FIELD OF THE INVENTION

The present invention pertains to thermal hair treatment methods and formulations for thermal hair treatment.

BACKGROUND OF THE INVENTION

Hair styling and treatment systems use high concentrations of caustic and/or reducers and oxidizers to permanently wave or straighten the hair by rearranging disulfide linkages. The Brazilian keratin method uses free aldehydes, like formaldehyde, gluteraldehyde or other mono and dialdehydes to crosslink or bind hydrolyzed proteins to the hair cuticle. Recent improvements, like the Coppola method in United States Patent Application 20090211593, complexes aldehydes in Schiff-base or other similar reactive keratin complexes that initially have lower free aldehyde present, but always contain some free aldehydes in the formulation prior to being applied to hair. Furthermore, the nature of the complexed aldehydes allows for a significant amount of aldehyde to be released during the thermal process of flat ironing the hair. Long term occupational exposure to aldehydes is generally considered undesirable. Scalp exposure to aldehydes and other treatment chemicals also may induce allergic reactions or irritation to individuals. One treatment method often referred to as the Japanese treatment, for example, relies on lye and other harsh chemicals and is very high in pH.

Mercapto-silicones of specific amounts of functionality have been used in hair care treatments as conditioners and styling aids, and even as intermediates for creating new styling polymers. U.S. Pat. No. 6,562,324 to Kumar et al, published May 13, 2003 required the free radical polymerization of ethylenically unsaturated monomers with a mercapto functional silicone as a chain transfer agent, thus forming an acrylate grafted polymer for improved curl retention as a fixative. No mention of high temperature thermal styling using a mercapto siloxane alone is provided. Kumar references the required number of mercapto functional groups on the mercapto functional silicone compound that will be reacted with monomers to form a graft polymer. It that invention, only the graft polymer serves as a styling aid, not a free mercapto siloxane. Furthermore, the —SH number reference is interpreted to be the relative number of SH groups acting as a chain transfer agent, thus implying that significantly less or no free mercapto functionality is remaining after the free radical polymerization is completed. Kumar further states if the number of mercapto functional groups on the mercapto functional silicone compound is too high, desired properties such as desirable sensational feeling in makeup cosmetics, and soft feel in hair care cosmetics will be lost. If the number of mercapto functional groups on the mercapto functional silicone compound is too low, desired properties such as style retention properties in hair care compositions may not be obtained. Lastly, it is taught that the SH equivalent weight of the mercapto functional silicone compound used as a chemical intermediate in free radical polymerization of ethylenically unsaturated monomers is preferably between 400-4000, and more preferably 1000-2000 and wherein the mole ratio of "silicone" monomer to "mercapto functional" silicone monomer "m/n" is 9-49. For such polymers, the description of desired property set is not directed to the intermediate mercaptan functional polymer, but rather to the acrylate-grafted mercaptan functional polymer of the invention.

Fridd in EP0295780 and Gee in EP-0829257 teach the use of mercapto functional silicones (non-modified) as an additive when treating hair with a composition containing an agent effective in reducing the disulphide linkages therein, e.g. ammonium thioglycollate. The hair is then arranged in the desired configuration and the disulphide linkages restored by application of an oxidizing agent. These methods require the redox cycle and also expose the scalp to high pH conditions.

Therefore alternative treatment methods are needed that produce excellent permanent or semi-permanent straightening results without damage to the hair, that are completely aldehyde-free, pH balanced to the scalp and do not have to rely on any harsh chemicals such as lye or a two part redox treatment to break and/or set disulfide linkages in the hair cortex.

OBJECT OF THE INVENTION

An object of the invention is to provide to new formulations for permanently straightening hair that produce excellent permanent or semi-permanent straightening results without damage to the hair, that are completely aldehyde-free, pH balanced to the scalp and do not have to rely on any harsh chemicals such as lye or a two part redox treatment to break and/or set disulfide linkages in the hair cortex.

A further object of the invention is to provide a new method of permanently straightening hair without damage to the hair, that is completely aldehyde-free, pH balanced to the scalp and does not have to rely on any harsh chemicals such as lye or a two part redox treatment to break and/or set disulfide linkages in the hair cortex.

SUMMARY OF THE INVENTION

The present invention provides formulations for lasting thermal straightening of hair where the straight set of the hair is retained after one or more shampoo cycles, as compared to daily conditioning or fixative treatments that are washed out after one shampoo treatment. The formulations comprise an effective amount of a silicone polymer that contains a high molar percent of mercapto-functionality, such that the silicone provides the hair with a straight, healthy appearance that is capable of retaining this preferred appearance over multiple hair-washing cycles with a typical shampoo treatment. The —SH equivalent weight of the mercapto functional silicone compound used is preferably less than 400, thus requiring a mole ratio of less than about 9, preferably less than 4 (whereby about a minimum of 25 mole percent mercapto-functional groups is the silicone polymer), more preferably less than 3 (greater than 30 mole percent mercapto-functional groups attached to the silicon polymer).

The formulations for straightening hair may optionally further comprise 1 to 10% by weight dimethylsulfone and 1 to 10% by weight urea.

The mercapto-silicone is a class of polymeric material with excellent adhesion to many surfaces and contains a reactive mercapto/thiol group typically linked to silicone via an alkyl group, —RSH. This good adhesion and flexibility of the polymer makes the mercaptosilicones useful as a traditional conditioning material in hair treatments. However, at low or even medium setting temperatures, such as using a blow dryer, curling iron or flat iron below about 350° F., even the polymers defined in this invention will not provide a satisfactory lasting set after one wash cycle when used at a level that does not otherwise detract from the condition of the hair. This lasting set is not achieved even though some of the polymeric material may still be visually present on the hair after the washing. This shows that adhesion of the polymer to keratin is important, but alone does not provide the properties of a lasting set. In contrast, setting hair with the polymers of this invention above about 350° F., surprisingly determined lasting set is possible after one or more wash cycles. Without wishing to be bound by theory, we believe the —SH group spontaneously covalently bonds to hair keratin protein and/or forms intra/intermolecular-crosslinks at the elevated temperature conditions present when flat ironing hair above 350° F. This additional bonding is possible because the thermal treatment is under conditions containing heated oxygen from air. It is thought that oxygen under this higher temperature condition further actives the —SH bond by auto-oxidation and can crosslink the polymer to a disulfide state, ultimately resulting in a more permanent bond on hair, than otherwise provided by the polymers adhesion at milder temperatures. Said hair keratin fibers contain a significant amount of —SH functionality in the form of cysteine amino acids found in the protein structure. Such keratin SH groups bond directly to the mercapto-silicone under auto-oxidative conditions. The addition of hydrolyzed keratin proteins further enhances the straightening effect by forming a filler additive that more deeply cements the cuticles closed during the thermal treatment by the same mechanism. The hydrolyzed keratin protein or derivative thereof is present in an amount of up to 10% by weight of the formulation, preferably 0.2 to 6% by weight of the formulation.

Not all mercaptosilicones work well in providing a lasting set. It has been found that application of a mercaptosilicone of an equivalent weight of mercapto functionality of less than about 400, directly to hair and hot ironing it at a temperature above about 350° F. is all that is required in the simplest sense to provide straightening effects capable of lasting up to eight wash cycles or more. Except for the proviso of the mercaptosiloxane, the application and flat ironing styling treatment method of this invention is similar to that used in the Brazilian keratin treatment or even the Coppola treatment, except that no aldehydes (as in the Brazilian method), or as aldehydes in Schiff base form (as per the Coppola method) are required. The exact nature of the mercaptosilicone that is preferred will be further delineated below. Formulating the mercaptosilicone into an anhydrous solvent system, or more preferable as an aqueous suspension or emulsified delivery system, is preferred since such dilution is capable of providing a more consistent application and one that can further enhance the sensory properties of the application by evenly controlling the amount of polymer coating and providing other conditioning ingredients. Most preferred is an aqueous delivery system that contains hydrolyzed keratin or derivatives thereof and a fragrance to mask any residual odor. The formulation can optionally further comprise silanes or other silicone that do not contain mercapto-functionality, including but not limited to amino-functional silicone compounds, cyclomethicones, dimethicones, dimethicone copolyols, fluorosilicones, phenyl silicones, phenyl trimethicones, one or more additional conditioning agents, emulsifiers, glycols, alcohols, and such common typical ingredients used in both conventional and thermal conditioning of hair. Fluorosilicones and fluoroalkylsilanes are particular preferred as the yield a hydrophobic texture.

Other stabilizers, fragrances, coloring agents, and the like may be present. Substantially aldehyde-free compositions may be used to fragrance the formula and assist in desirable reactions with the hair of the subject according to the treatments methods of the present invention. Mercapto-silicones have an inherent malodor, so adding fragrance is desirable and effective in masking the odor. The heat process also removes most of the odor, so surprisingly little fragrance is required to make the treatment fully cosmetically acceptable. The treatment methods generally comprise substantially uniform application of a formulation of the present invention to the hair of a subject, followed by elevating the temperature of the formulation on the hair by, for example, use of a hot hair iron. Removal of excess formulation by combing, toweling or washing the hair is also possible. While this invention is indeed preferably aldehyde free, we hereby mention the utility in combining it with other prior treatments that do contain aldehydes or the Schiff-bases of aldehydes to yield a hybrid system that combines performance attributes of the invention with otherwise compatible existing technology. Also, since auto-oxidation is an important vital element to locking in the lasting set and it occurs only at elevated temperature to cure the system to its optimum condition, we believe that a optional oxygenated materials or even oxidizers could be added as a catalyst during the application process to modify the cure state, cure conditions or lessen the level of smoke emitted, similar to the art of providing oxygenated fuels for a more efficient combustion process. While a possible two part system is included as an embodiment of this invention, the overall spirit and objective of this invention was to avoid harsh chemicals, so the one part system without added oxidizer or added aldehydes is always preferred.

The preferred added keratin may be hydrolyzed from wool or human hair by acid or enzymatic means to form a soluble keratin. Wool protein source is preferred. It may also be hydrolyzed and ionized in the manner as described in the Coppola art in United States Patent Application 20090211593, specifically those keratins without aldehydes.

If a two part system is so desired, the second part may optionally contain an oxidizer such as peroxides or benzoquinone. An oxidizer is not a required embodiment to this invention. The thickening agent may be any gum such as neutralized carbomers, modified cellulosics like Hydroxyethylcellulose (HEC) or Polyquaterium-10, or a cationic gum like modified guar gum. The kinematic viscosity of the formulation, as measured with a Brookfield viscometer at 60 rpm and at 25° C., may be between about 50 to about 5000 centipoise, about to be sprayed on or applied as a lotion.

Essentially, the mercaptosilicone is formulated into any conditioner that has a pH between 3-7, preferably it is in the range that is pH balanced to the hair or slightly on the acid side for a glossy appearance of the hair cuticles and best stability of the mercapto-polymer. The nature of the other ingredients in the formula are widely flexible and those skilled in the art may choose those from a wide assortment of ingredients that promote gloss, emulsify the silicones, provide a light feel, form the lowest possible process smoke and do not otherwise detract from the performance of the mercaptosilicone. While the mercaptosiloxane polymer could be applied 100% neat or in concentrated form to hair, the preferred amount is in an aqueous emulsion at about 0.5-10% by weight and more preferably about 2-6% by weight of polymer for a salon type product. Products formulated at the lesser amount of the range are more suitable for home and daily use to avoid build-up during more frequent applications.

The product formula is massaged into dry clean hair, allowed to set for a few minutes, gently blow dried and then flat ironed in sections to achieve a lasting set. The heat styling treatment uses a hot flat iron instrument as typical for the Brazilian Keratin treatment at above 350° F. and below 450° F. If the formula is dilute, the application process can be repeated in small intervals to achieve a final conditioning level desired by the stylist.

DETAILED DESCRIPTION OF THE INVENTION

The Mercapto Siloxane

Linear mercaptosilicones of the present invention are represented by the following formula:

where R' denotes a hydroxyl group, hydrogen, an alkyl group of 1-4 carbon atoms or a phenyl group provided at least 50 percent of the total number of R' groups are methyl. Q denotes a mercapto functional substituent —R"SH where R" is a divalent alkylene radical of 3-6 carbon atoms; z is 0 or 1; x has an average value of 0-100; y is 0-100 when z is 1, and y has an average value of 1-50 when z is 0. The invention requires that at least 25 mole percent of silicon atoms have a Q group attached.

Suitable R' groups are methyl, ethyl, propyl, isopropyl, butyl, isobutyl, and phenyl. The alkylene radicals R" include trimethylene, tetramethylene, pentamethylene, —CH$_2$CHCH$_3$CH$_2$—, and —CH$_2$CH$_2$CHCH$_3$CH$_2$—. Silicones where R" is a trimethylene or an alkyl substituted trimethylene radical such as —CH$_2$CHCH$_3$CH$_2$— or —CH$_2$CH$_2$CH$_2$— are preferred.

When z is zero, the silicone polymer has only pendent mercapto functional substituents in the polymer chain. When z is one, the silicone polymer may have only terminal mercapto functional substituents, or both terminal and pendent mercapto functional substituents in the polymer chain. While x can have a value greater than 100, i.e., up to 4,000 for example, preferably x varies from 0-100, and y varies from 0-100 when z is one and from 1-100 when z is zero. Most preferably, the value of x+y is about 5-200.

The mercapto functional silicone may be a linear polysiloxane as delineated above or a branched-chain polysiloxane. Linear polysiloxanes correspond to the structural type MD$_n$M or R$_3$SiO(R$_2$SiO)$_n$SiR$_3$. Branched-chain polysiloxanes contain at least one trifunctional RSiO$_{3/2}$ or tetrafunctional SiO$_{4/2}$ siloxane unit as a branching center. The branching unit is incorporated into the chain.

An example of a linear polysiloxane is:

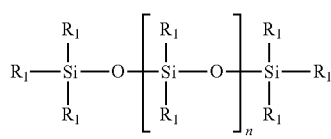

For this example, R1 is methyl, phenyl or mercaptopropyl functional group.

An example of a simple branched-chain polysiloxane is:

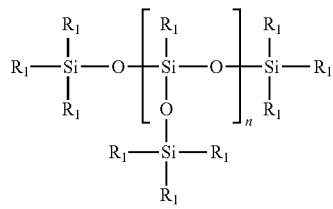

As shown, a branch chain siloxane polymer is a mixture of monofunctional silicone (M-type) and trifunctional silicone (T-Type) and are called M-T siloxanes.

Preferred M-T mercapto silicones include those where the R group on the T-siloxane is methyl:

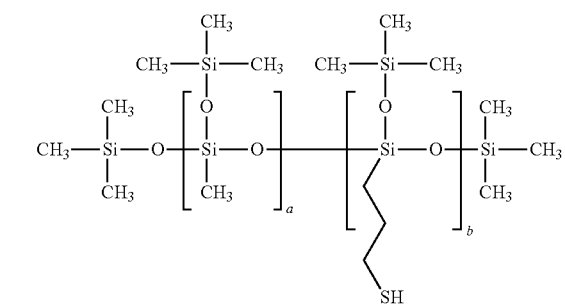

and those where the R group on the T-siloxane is phenyl:

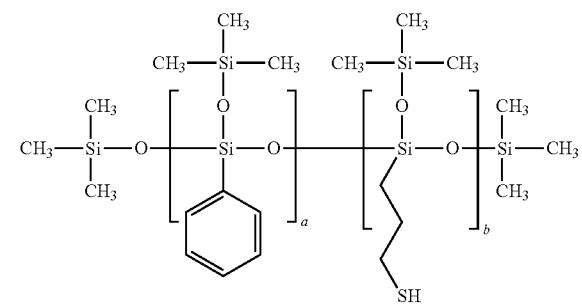

Also preferred are M-T polymers where the T-siloxane R-group is a random mixture of methyl and phenyl.

More complex branched-chain polysiloxane are possible by combining both linear (D) and branched (T) siloxane groups. Some tetrafunctional (Q-type) siloxane groups may also be present in small quantities in the more complex polysiloxanes, with the caveat that the amount of T or Q groups present are not sufficiently high in ratio to the M groups such that the viscosity of the final polymer remains low enough to remain a flowable liquid at room temperature.

The preferred mercapto-siloxane polymers contain ratios of a:b are about 9:1 to about 0:1.0. Even more preferred is when b is over 50 mole % and the mercaptosiloxane monomer property becomes the dominant chemical entity on the polymer.

The mercapto siloxanes of the present invention may be prepared from existing published methods by using either solution or emulsion polymerization techniques. Solution polymerization techniques are preferred because the methanol or ethanol by-products and low boiling oligomers may be preferably distilled off to yield a product of defined molecular weight. U.S. Pat. No. 4,238,393 (Takamizawa et al) provides a method of making linear mercapto siloxanes such as the homopolymer and dimethicone block copolymers thereof. Solution polymerization and concurrent high temperature distillation is preferred because it yields a polymeric product that has significantly lower odor from residual sulfur containing by-products and smokes less during application at elevated temperatures in comparison to a non-distilled product. Hydrosilation of allyl sulfur containing monomers that yield a mercapto polysiloxane is also a useful and economical route to making this class of polymers.

The method of applying the mercapto-siloxane of the present invention includes the following steps:

a) applying a formulation containing a mercapto siloxane to clean hair, preferable clean and dry hair, whereby said formulation may contain any number of other optional ingredients to form a stable emulsion or solvent based delivery system for the mercaptosiloxane and where said formulation may preferably contain a keratin derivative; and b) elevating the temperature of the formulation on the hair to cause the mercaptosiloxane to react with the hair, whereby the reaction acts to maintain a straight hair style of more than one wash cycle and preferably more than eight wash cycles.

In one aspect, the invention provides a system for hair-straightening system that does not require any aldehyde or oxidizing or bleaching chemicals. In another aspect, the systems and formulations of the present invention differ over the prior art in their mechanism for interaction with hair, whereby the mercaptosiloxanes is reacting to the hair under the conditions of elevated temperature in air, thereby crosslinking to the hair cuticle and/or hydrolyzed keratin protein filler, thus forming an impenetrable polymeric film that prevents excess moisture from entering or exiting the hair cortex, thus holding the desired shape of the hair during washing or during exposure to high humidity environments. In this embodiment, the use of hot irons and other tools in combination with the formulations of the present invention can provide semi-permanent straightening of curly, frizzy, or damaged hair as well as providing increased sheen and beauty to the hair. Although this invention is completely aldehyde-free, it does not preclude the inclusion of aldehydes as common fragrance additives or as additives for other purposes in the formula as optional ingredients.

Among the advantages and benefits that can be achieved in embodiments of the present invention are:

1. A hair treatment which does not expose hair to harsh chemicals such as oxidizing agents or aldehydes;
2. A method of thermal hair treatment which employs a controlled crosslinking reaction using mercaptosiloxanes that can be as effective of a treatment relative to existing processes using aldehydes;
3. A treatment solution and method which allows for swimming or washing of the hair immediately after treatment with any shampoo, including sulfate containing shampoos;
4. A treatment solution and method which adds shine and flexibility to hair by the application of mercapto silicone, preferably a phenyl containing mercapto silicone;
5. A solution and method for treating all hair types, including curly or damaged hair; and
6. A solution and method that can be applied periodically in a salon or at home, whereby such period or interval is mainly dependent on polymer concentration, for example without limitations, once a month or once a week (or even once a day when the formula is essentially fully diluted).

The keratin protein may comprise a keratin hydrolysate formed by any known method, such as those delineated in United States Patent Application 20090211593 by Coppola.

Other (non-mercapto) Silicone Compounds and Conditioning Agents The formulation of the present invention may comprise an amine-functional silicone neutralized to a pH less than 7, to enhance the interaction of conditioning agents with the hair. Amine-functional silicones can include aminopropyl phenyl trimethicone, amino bispropyl dimethicone, aminopropyl dimethicone, amodimethicone, and amodimethicone hydroxystearate. The amino groups of amino-functional silicones are particular useful in attaching the compound to damaged hair that has become relatively hydrophobic, thereby increasing the affinity of the hair for other conditioning agents. A variety of known conditioning agents can be added such as behenoxy dimethicone, C30-45 alkyl dimethicone, C24-28 alkyl dimethicone, C30-45 alkyl methicone, cetearyl methicone, cetyl dimethicone, dimethoxysilyl ethylenediaminopropyl dimethicone, hexyl methicone, hydroxypropyldimethicone, stearamidopropyl dimethicone, stearoxy dimethicone, stearyl methicone, stearyl dimethicone, vinyl dimethicone, and the like. Vinyl dimethicones may react with the mercapto-siloxane under certain conditions and created unwanted gelation, so their optional use may require added formulation techniques such as a two part delivery system.

Non-silicone conditioning agents can include natural extractives and oils such as Jojoba oil extract, Vitamin E oil, emu oil, avocado oil, and the like. Fatty-acid derivatives maybe used such as poly-glyceryl laurates (e.g., poly-glyceryl-laurate 10), as well as related stearates, palmitate, oleates, and the like.

Cationic conditioning agents like cetyltrimonium halide or behentrimonium halide may also be used in this invention. A wide variety of surfactants and emulsifiers may be used to deliver the mercapto siloxane from oil-in-water emulsions. Emulsifiers such as alkyl glucosides, alkyl ethoxylates, and sorbitan ethoxylates are useful for this purpose. Examples include but are not limited to decyl glucoside, laureth-4 to laureth-23, polysorbate 80 and polysorbate-20, used singly or in combination.

Optionally, oxidizers such as benzoquinone, other quinone derivatives including hydroquinone and aminoquinones (e.g., those of U.S. Pat. Nos. 4,023,926; 3,919,265 or 2,267,741), suitable peroxides, and the like, may participate in polymerization reactions similar to the tanning reactions known involving quinones and collagen or other proteins. Such oxidizers may thereby assist in the formation of a sealing layer around the hair shaft, participating with the mercapto-siloxanes, the silicone fluids such as cyclo-dimethicone and amino-functionalized silicones, and sulfur groups from the ionized keratin derivative or the hair itself. Liquid oxidizers like hydrogen peroxides should be applied in a two component system whereby the peroxide is packaged separately from the mercapto-siloxane and optional keratin protein, if used. Oxygenated materials are generally useful for lowering the smoke generated during the hot iron process.

The formula is applied to hair, preferably clean dry hair, in such a manner as typical of applying a leave-in conditioner using the hands, a brush or other applicator means. The salonist will typically divide a subjects' hair into smaller tress sections for a more controlled application and coverage pattern. A solution comprising a formulation of the present invention is applied, such as one according to the exemplary formulations. The solution is combed into the hair for maximum coverage and allowed to sit for anywhere from one minute to 20 minutes. The hair with product can be surface dried using a blow dryer to speed up the application process and cause less damage to the hair from steam exiting the hair when heated. Use of a hot flat iron is required to seal the mercapto polymer onto the hair surface. Suitable temperatures for the iron may, for example, be about 350° F. or greater, such as from about 350° F. to about 450° F., preferably from about 380° F. to about 420° F. The elevated temperature causes the mercapto-siloxane to react with the hair and/or with the keratin to seal the hair shaft. The hot iron may be applied several times, such as from 5 to 10 times, while also combing the hair with a fine-toothed comb. Excess formula may be removed from the hair with a surface towel treatment. If coverage is deemed excessive, the hair may be immediately washed and dried to remove any excess material. The application of the formulations of the present invention may be enhanced with any known methods in the art.

EXAMPLES

Example 1

Uncapped Gamma-Mercaptopropyl, Methylpolysiloxane Homopolymer:

To a five neck 500 ml reactor equipped with nitrogen inlet, condenser, stirrer and temperature probe and addition funnel, was added 50 ml $H_2O$ containing 0.070 g concentrated HCl. 180 g mercaptopropyl, methyldimethoxysilane was added dropwise over 30 minutes to the reactor and allowed mix for 5 hours. The reaction exothermed slightly during the silane addition.

The reaction product was transferred to a separation funnel and the aqueous phase removed. The silicone phase was washed and separated with 50 ml water and 200 ml toluene. Some NaCl was added to form a clear separation layer. The toluene layer was washed 2× more time in the same manner with added water before being dried over excess anhydrous magnesium sulfate and filtered. The toluene was distilled off between 70° C.-150° C. A vacuum distillation at 150° C. removed any light ends to yield 125.5 g of an oily product with a density of 1.10 g/ml. This polymer is ~100 mole % mercapto-functional.

Example 2

0.1 g of the product of example 1 was dissolved in 1 g. isopropyl alcohol and applied to a dry 2.5 g. frizzy/curly hair tress, massaged in and combed with a fine toothed comb. The tress was then flat ironed 10 times with a Babylys styling iron set at 400° F. The tress was thin and straight and conditioned. The smoke generated during hot combing was medium high and required proper ventilation. It was allowed to cool and then immediately washed for eight cycles using Suave daily clarifying shampoo containing sulfate-type surfactants. It was completely dried using a blow dryer after the $1^{st}$, $4^{th}$ and $8^{th}$ cycle. The tress was completely thin and straight after all 8 wash dry cycles. A second tress was similarly processed, but at only 325° F. It failed after the first wash cycle, thus showing temperature dependence.

Example 3

In a manner similar to that of example 1, a dimethyl, mercaptopropylsiloxane copolymer containing about a 1:1 mole ratio of mercapto-functional silicone to methyl functional silicone was prepared by condensing and equilibrating mercaptopropylmethyldimethoxysilane, hexamethyldisiloxane and dimethyldimethoxy silane. The product was slightly turbid oil that is characterized as 50 mole % mercaptofunctional, calculated to be between about 12-13% SH group.

Example 4

The tress-test method of example 2 was repeated except using the product of example 3. The tress remained straight after 8 wash cycles. The smoke generated during hot combing was medium high.

Example 5

In a manner similar to that of example 3, a phenyl, mercaptopropyl siloxane polymer containing about a 1:1 mole ratio of mercapto-functional silicone to phenyltrimethicone-functional silicone was prepared by condensing and equilibrating mercaptopropylmethyldimethoxysilane, hexamethyldisiloxane and phenyltrimethoxysilane. The product was a slightly turbid oil with a refractive index of 1.51 and is 50 mole % mercaptofunctional, calculated to be between about 12-13% SH group. The product was distilled at a higher temperature of 170° C.

Example 6

The tress-test method of example 2 was repeated except using the product of example 5. The tress remained straight after 8 wash cycles. The amount of smoke generated during flat ironing was significantly less than example 4. The gloss on the hair tress was higher than example 4.

Example 7

The tress-test method of example 2 was repeated, but this time 0.1 g. of a commercial polyacrylate-mercaptosilicone polymer from 3M (polymer VS-80 dry) was diluted into 1 g isopropanol and the entire amount applied to the hair tress and hot ironed. The ironing procedure was not able to be completely finished due to excessive drag on the hair and had very undesirable aesthetics as the tress was too sticky and straw like to process in a cosmetically acceptable manner. The tress had evidence of residual product bonded to the hair surface after one wash cycle, but otherwise failed the one wash cycle due to incomplete set. This experiment showed the prior art acrylate mercaptosiloxane polymer, derived from mercaptosiloxane and having only a nominal amount of free mercapto group present, performed completely different than the inventive system and acted more like a sticky, hydrophobic polymer than thermal setting agent in this test and is not suitable as the main component for a thermal straightening application.

Example 8

A dimethyl, mercaptopropylsiloxane copolymer was prepared similar to the manner of Example 3 except the final —SH content was reduced to only 2%. The molar ratio of dimethyl silicone to mercapto silicone was about 20:1. The tress-test procedure of example 2 was performed on 0.1 g of this polymer in 1 g isopropyl alcohol. The tress failed to maintain full straightness after one wash cycle and the remaining wash cycles were abandoned.

Example 9

A dimethyl, mercaptopropylsiloxane copolymer was prepared similar to the manner of Example 3 except the final —SH content was 5.5%. The molar ratio of dimethyl silicone to mercapto silicone was about 6:1. The tress-test procedure of example 2 was performed on 0.1 g of this polymer in 1 g isopropyl alcohol. The tress maintained full straightness after one wash cycle, but began to show failure after the 4$^{th}$ wash cycle.

Example 10

The example 6 was repeated in a general sense with two tresses, except after the polymer solution was applied to the sample tresses, then immediately over-coated with 0.5 g of 4% $H_2O_2$ aqueous catalyst solution and processed with the flat iron as usual. The first of the two tresses was immediately rinsed with 10 ml deionized water and the solution captured and tested for residual peroxide. The rinse solution tested negative for residual peroxide, thus indicating the hot iron step completely decomposed the peroxide in-situ. The second tress was shampoo cycled as before and the tress maintained full straightness after eight wash cycles. The smoke produced during the flat iron procedure was significantly reduced compared to Example 6, thus indicating an oxygen catalyst source is beneficial to the overall process. The color of the tress was not altered compared to example 6.

Example 11

The following emulsion was created and tested in the hot iron tress test:

| Phase | Ingredient | Weight % |
|---|---|---|
| A | Product of example 3 | 5 |
|   | Polysorbate-20 | 1 |
|   | Fluorosilicone (Gransil DM-100) | 0.5 |
|   | Peg-12 dimethicone | 0.2 |
|   | Keratin Protein | 0.25 |
|   | Fragrance | 0.13 |
|   | 1,3 Butylene Glycol | 5 |
| B | Water | 87.7 |
|   | Carbomer | 0.2 |
| C | TEA | (to pH 5) |
| D | Preservative | qs |

Procedure: Combine Phase A, turn on homogenizer and add Phase B to Phase A, Neutralize with Phase C and finish with Preservative D.

This emulsion is an example of a hair treatment formula of the current invention. It was applied to hair tresses at varying loadings and after running multiple tress test experiments, it was found to be capable of retaining a straight style beyond 1 wash cycle. Generally when the level was adequate to survive one cycle, it often also survived the four and eight wash cycles. This level was approximately 1 g. application of this emulsion to about 2.0-2.5 grams of hair. Results varied depending on hair condition, but it was determined that hot ironing smaller sections of hair resulted in more even application and lasting style. Hair tresses with evidence of split ends or extreme curls toward the ends required higher application levels on these problem areas compared to the healthier root area. This formula demonstrates a cosmetically acceptable formula that begins to balance tress aesthetics with performance and can be used as often as required to maintain a lasting straight hair set without undo damage to the hair.

The inventors feel that this formula as illustrated can be further refined by following the teaching set forth herein, including making the polymers of slightly higher molecular weight and distilling said polymers at temperature approaching that of the hot iron application, such that oligomers that tend to form volatile smoke are removed by and large form the system before the hot application. We also acknowledge the benefit of using highly oxygenated compounds as additives to further reduce the smoke generated by the hot application.

What is claimed is:

1. A formulation useful for semi-permanent thermal conditioning and straightening of the hair consisting of
   a) 0.1% to about 100% by weight of a mercaptosilicone of the following formula:

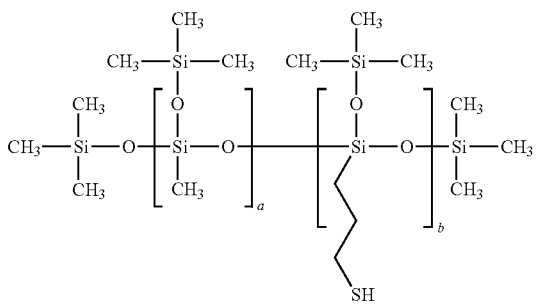

or a mercaptosilicone of the following formula

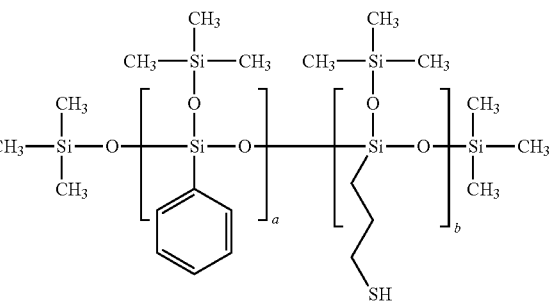

wherein a and b are in a weight ratio of about 9:1 to about 0 to 1.0,
   b) hydrolyzed keratin protein in an amount of 0.2 to 6% by weight of the formulation
   c) thickening agent in an amount of 0.2 to 6% by weight of the formulation
   d) 1 to 10% by weight dimethylsulfone and/or 1 to 10% by weight urea
   e) non-mercapto containing silicones.

2. The formulation of claim 1 that is an aqueous formula.

3. The formulation of claim 1 that is an anhydrous formula.

4. The formulation of claim 1, wherein the thickening agent is cationic or nonionic and wherein the formulation has a kinematic viscosity of between about 10 to about 5000 centistokes.

* * * * *